(12) United States Patent
Hurlebaus et al.

(10) Patent No.: US 7,824,480 B2
(45) Date of Patent: Nov. 2, 2010

(54) AIR TREATMENT SYSTEM

(75) Inventors: Randy W. Hurlebaus, Waunakee, WI (US); Curtis J. Scadden, Waunakee, WI (US); Curtis Leroy Cruver, IV, Elmhurst, IL (US); Chris Rieger, Madison, WI (US); James E. Pelkey, Verona, WI (US); Ronald M. Austin, New Glarus, WI (US); Mark J. Blahnik, Sun Prairie, WI (US); Colin R. Clerkin, Waunakee, WI (US); Brian Wylie, Stoughton, WI (US); Thomas Haft, Madison, WI (US)

(73) Assignee: Sub-Zero, Inc., Madison, WI (US)

( * ) Notice: Subject to any disclaimer, the term of this patent is extended or adjusted under 35 U.S.C. 154(b) by 375 days.

(21) Appl. No.: 11/801,004

(22) Filed: May 7, 2007

(65) Prior Publication Data

US 2008/0168790 A1 Jul. 17, 2008

Related U.S. Application Data

(63) Continuation-in-part of application No. 11/654,442, filed on Jan. 17, 2007.

(51) Int. Cl.
*A61L 9/20* (2006.01)
(52) U.S. Cl. .............................. 96/224; 96/223; 62/78; 422/121; 422/122
(58) Field of Classification Search ................. 96/224, 96/226, 223; 62/78, 264, 314; 422/120–122
See application file for complete search history.

(56) References Cited

U.S. PATENT DOCUMENTS

| 2,288,587 | A | * | 6/1942 | Kalischer ..................... 62/227 |
|---|---|---|---|---|
| 4,108,363 | A | | 8/1978 | Susumu |
| 4,954,465 | A | | 9/1990 | Kawashima et al. |
| 4,955,203 | A | | 9/1990 | Sundhar |
| 4,955,208 | A | * | 9/1990 | Kawashima et al. .......... 62/264 |
| 5,006,248 | A | | 4/1991 | Anderson et al. |
| 5,035,784 | A | | 7/1991 | Anderson et al. |
| 5,062,272 | A | | 11/1991 | Burns |
| 5,078,971 | A | * | 1/1992 | Matuda et al. ............... 422/121 |
| 5,135,645 | A | | 8/1992 | Sklenak et al. |
| 5,227,342 | A | | 7/1993 | Anderson et al. |
| 5,230,220 | A | * | 7/1993 | Kang et al. .................... 62/78 |
| 5,255,530 | A | * | 10/1993 | Janke ......................... 62/180 |
| 5,836,669 | A | | 11/1998 | Hed |
| 5,919,422 | A | | 7/1999 | Yamanaka et al. |
| 6,228,502 | B1 | | 5/2001 | Saitoh et al. |
| 6,286,330 | B1 | | 9/2001 | Kopf |
| 6,328,937 | B1 | | 12/2001 | Glazman |

(Continued)

OTHER PUBLICATIONS

Sub-Zero Design Guide, 3758546 Rev-B, Sep. 2006, 84 pages.

(Continued)

*Primary Examiner*—Michael A Marcheschi
*Assistant Examiner*—Robert A Clemente
(74) *Attorney, Agent, or Firm*—Foley & Lardner LLP

(57) ABSTRACT

A storage compartment comprises an enclosure defining a storage space and an air treatment system in fluid communication with the interior space. The air treatment system includes a light source and a catalyst and configured to treat air without the use of ozone.

19 Claims, 11 Drawing Sheets

U.S. PATENT DOCUMENTS

| | | | |
|---|---|---|---|
| 6,336,998 | B1 | 1/2002 | Wang |
| 6,346,143 | B1 | 2/2002 | McGowan |
| 6,581,394 | B1 | 6/2003 | Smolenskiy |
| 6,606,869 | B2 | 8/2003 | Takahashi et al. |
| 6,658,884 | B2 * | 12/2003 | Takahashi et al. ............. 62/264 |
| 6,736,885 | B2 | 5/2004 | Kaiser |
| 6,865,896 | B2 * | 3/2005 | Kaji et al. ...................... 62/78 |
| 6,866,828 | B2 | 3/2005 | Segawa et al. |
| 6,918,259 | B2 | 7/2005 | Anderson et al. |
| 6,923,015 | B2 | 8/2005 | Ueno et al. |
| 7,040,101 | B2 * | 5/2006 | Takeda et al. ................. 62/78 |
| 7,056,476 | B2 | 6/2006 | Okada et al. |
| 7,083,725 | B2 | 8/2006 | Jenkins, Jr. et al. |
| 7,143,591 | B2 * | 12/2006 | Nonaka et al. ................ 62/129 |
| 7,377,125 | B2 * | 5/2008 | Seiden et al. ................. 62/441 |
| 2003/0046947 | A1 * | 3/2003 | Ohya et al. .................... 62/264 |
| 2006/0080994 | A1 * | 4/2006 | Seiden et al. ................. 62/441 |
| 2007/0107452 | A1 * | 5/2007 | Kim et al. ..................... 62/264 |
| 2007/0157646 | A1 * | 7/2007 | Kim et al. ..................... 62/187 |
| 2007/0209373 | A1 * | 9/2007 | Taira et al. .................... 62/78 |
| 2007/0266725 | A1 * | 11/2007 | Anikhindi et al. ............. 62/317 |

OTHER PUBLICATIONS

Toshiba Corporation, Toshiba Review 2001, vol. 56, No. 12, "'Hikari Plasma Senzohko:', Model GR-473K Refrigerator," p. 8, bearing a designation "2001".

Toshiba Corporation, "'Hikari Plasma Senzohko; Model GR-473K Refrigerator," pp. 64-67, bearing a designation vol. 56, No. 12 (2001).

* cited by examiner

AIR TREATMENT SYSTEM

CROSS REFERENCE TO RELATED APPLICATIONS

This application is a continuation-in-part of prior U.S. application Ser. No. 11/654,442, filed Jan. 17, 2007, the content of which is incorporated herein by reference in its entirety.

BACKGROUND

The present invention relates to an air treatment system. More specifically, the present invention relates to an air treatment system that may be provided in a variety of locations in conjunction with a storage compartment or other device.

Storage compartments such as refrigerated and non-refrigerated storage compartments and appliances are generally known. It is generally known to provide an air treatment system for such compartments. Known air treatment systems typically include a purification/filtration element and a fan to force air through the purification/filtration element. Also, known systems are often mounted on a wall inside the compartment. However, such known air treatment systems have several disadvantages including waste of storage space, limited performance due to inadequate access to air and air flow (especially, e.g., when the food storage space is relatively full with food products, etc.), and having to pass a power cord through the refrigerator wall to power the fan. It is also known to provide a purification/filtration element that uses a combination of titanium dioxide, ultraviolet light, and ozone. However, use of ozone in such a combination tends to degrade or be harmful to the material around it and to food in the storage compartment.

Accordingly, it would be advantageous to provide an improved air treatment system for a storage compartment. It would also be advantageous to provide an air treatment system that may be integrated into the air flow of a storage compartment in a variety of locations. It would further be advantageous to provide an air treatment system for a refrigerated compartment that only treats (e.g., purifies, filters, etc.) a portion of the air passing from the evaporator to the evaporator fan. It would further be advantageous to provide an air treatment system with a cartridge and/or other subcomponents that are accessible to be removed, replaced, recharged, repaired, maintained, or the like in an independent fashion. It would further be advantageous to provide an air treatment system with a purification/filtering element that does not use ozone. It would be desirable to provide for an air treatment system having one or more of these or other advantageous features. To provide an inexpensive, reliable, and widely adaptable air treatment system that avoids the above-referenced and other problems would represent a significant advance in the art.

SUMMARY

The present invention relates to a storage compartment comprising an enclosure defining a storage space and an air treatment system in fluid communication with the interior space, the air treatment system comprising a light source and a catalyst and configured to treat air without the use of ozone.

The present invention further relates to an air treatment system for an appliance comprising a housing comprising an inlet and an outlet and defining a conduit, a light source provided within the housing, a catalyst provided within the housing, and a connector configured to removably couple the housing to the appliance.

The present invention further relates to an appliance comprising an enclosure defining a cooled space having a first portion and a second portion at least partially separated from the first portion, and an air treatment system configured to treat air received only from the first portion and release the treated air to one of the first portion and the second portion.

The present invention further relates to an appliance comprising an enclosure defining an interior space and an air treatment system in fluid communication with the interior space and configured to treat air utilizing an ultraviolet light source in combination with a titanium dioxide coated catalyst and without the use of ozone, wherein the air treatment system is configured to operate on an intermittent basis based upon at least one input.

The present invention further relates to various features and combinations of features shown and described in the disclosed embodiments. Other ways in which the objects and features of the disclosed embodiments are accomplished will be described in the following specification or will become apparent to those skilled in the art after they have read this specification. Such other ways are deemed to fall within the scope of the disclosed embodiments if they fall within the scope of the claims which follow.

Figure 1:
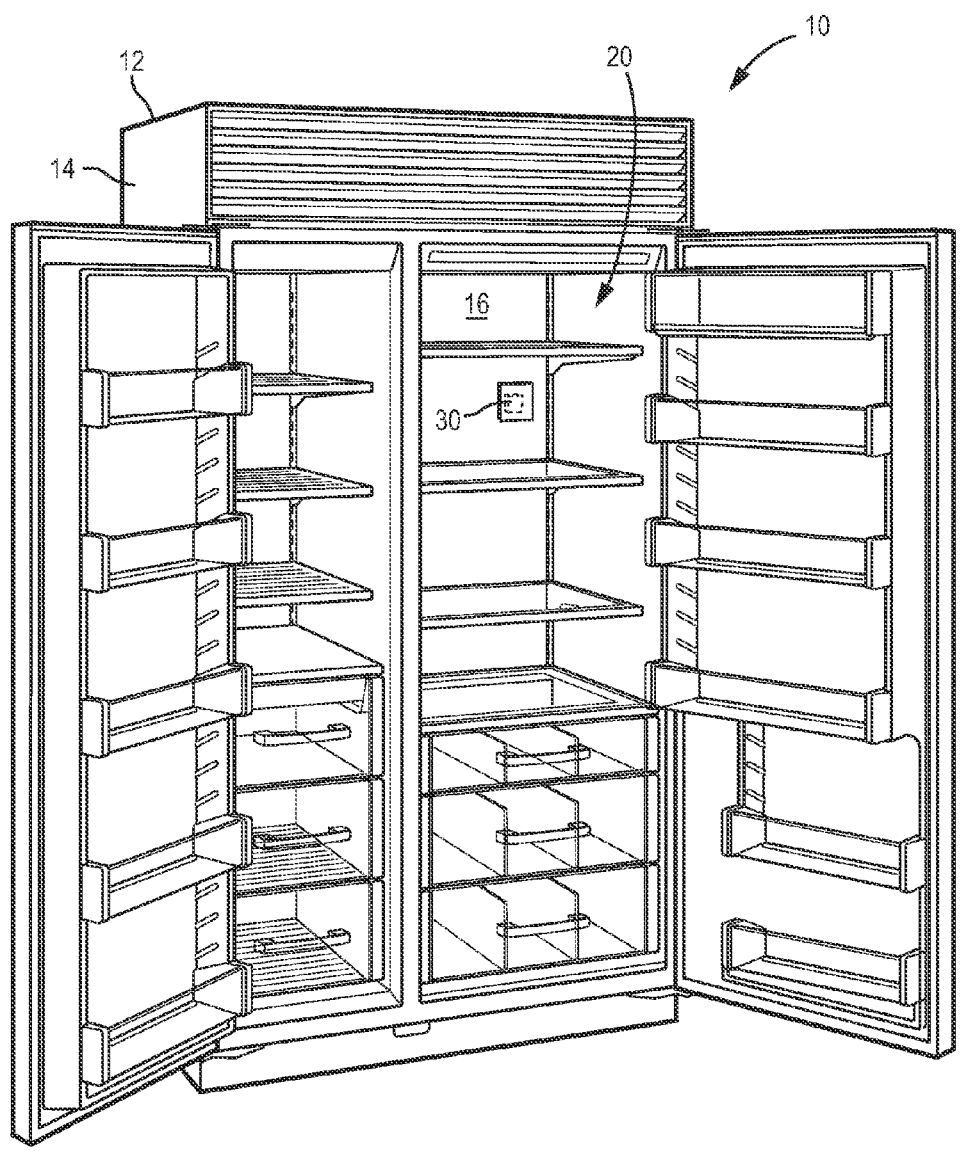
FIG. 1 is a perspective view of a refrigerator including an air treatment system according to an exemplary embodiment.

Before explaining a number preferred, exemplary, and alternative embodiments of the invention in detail it is to be understood that the invention is not limited to the details of construction and the arrangement of the components set forth in the following description or illustrated in the drawings. The invention is capable of other embodiments or being practiced or carried out in various ways. It is also to be understood that the phraseology and terminology employed herein is for the purpose of description and should not be regarded as limiting.

DETAILED DESCRIPTION OF THE PREFERRED AND EXEMPLARY EMBODIMENTS

FIG. 1 shows an appliance as a refrigerator 10 according to a preferred embodiment. Refrigerator 10 includes an enclosure 12, an evaporator 22, an evaporator fan 24, and an air treatment system 30. Enclosure 12 forms the main body of refrigerator 10 and includes an insulated outer wall 14 and an inner wall 16 (e.g., cold plate, etc.). Enclosure 12 may be a refrigerator component (e.g., for fresh foods) or a freezer compartment (e.g., for frozen foods). Outer wall 14 and inner wall 16 are at least partially separated by an air duct 18 (e.g., passage, space, volume, passageway, etc.). Inner wall 16 defines a cooled area or compartment 20 that is configured to receive items to be kept cooler than the outside environment. Cooled area 20 is cooled by a refrigeration system that includes at least a compressor, an evaporator 22, and a first or evaporator fan 24. According to an exemplary embodiment, evaporator 22 is disposed at least partially in air duct 18 and generally towards the bottom of enclosure 12. Evaporator fan 24 is disposed towards the top of enclosure 12 and draws air from evaporator 22, upwards through air duct 18 and into cooled compartment 20.

Figure 2:
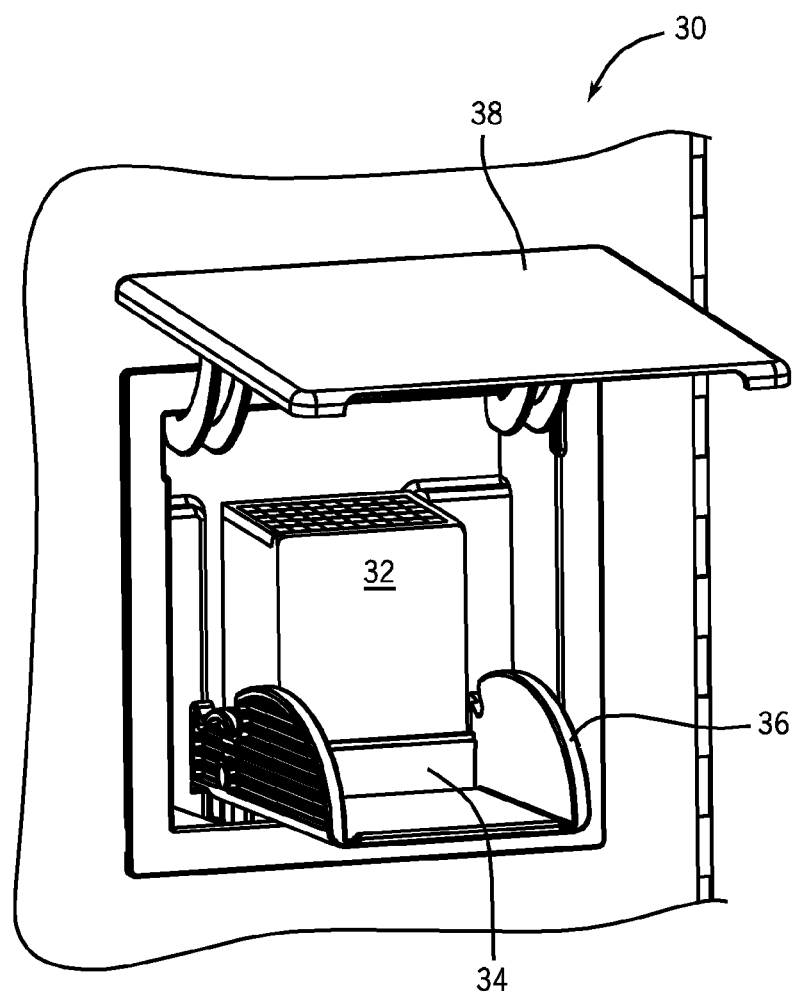
FIG. 2 is a more detailed perspective view of the air treatment system in FIG. 1 in an open position according to an exemplary embodiment.

According to an exemplary embodiment, air treatment system 30 is disposed between evaporator 22 and evaporator fan 24 and at least partially within air duct 18. Air treatment system 30 is configured treat (e.g., purify, filter scrub, freshen, etc.) air inside refrigerator by oxidizing odor, bacteria, ethylene, volatile organic compounds (VOC's) or other undesirable particles without the use of ozone. According to a preferred embodiment, air treatment system 30 includes a removable filter cartridge or module 32 that is received by a base 34 with the aid of a mounting mechanism 36. A second fan 35 is provided to facilitate directing airflow into air treatment system 30. An access panel 38 is provided on inner wall 16 to allow access to air treatment system 30 from cooled compartment 20. A mounting panel 39 is coupled to outer wall 14 and provides a mounting surface for base 34 and/or other components of air treatment system 30. While air treatment system 30 is shown in FIGS. 1 and 2 as being disposed towards one side of enclosure 12 and towards the top of enclosure 12 it should be understood that air treatment system 30 may be provided in a wide variety of locations between evaporator 22 and evaporator fan 24. A majority of air treatment system 30 is disposed within air duct 18 so that it does not occupy substantial space within cooled compartment 20 or extend a substantial amount outside outer wall 14. Air treatment system 30 is shown as being located downstream of evaporator 22 (e.g., between evaporator 22 and fan 24). Alternatively, the air treatment system may be in any of a variety of locations in the airflow (e.g., upstream) and the evaporator fan may be located upstream of the evaporator (e.g., to push or blow air across the evaporator).

According to an exemplary embodiment, filter cartridge 32 is a removable member that is configured to filter or treat air passing through it. Filter cartridge 32 includes an outer housing 40 that forms a passage that is generally aligned with the air flow in air duct 18. According to an exemplary embodiment, housing 40 includes a front 80, a back, 82, a bottom 84, and a top 86. Front 80 and back 82 are generally solid members while bottom 84 and top 86 includes a plurality of slots or openings that allow air to pass through housing 40. A catalyst and a lamp 44 are disposed within housing. According to an exemplary embodiment, the catalyst (not shown) is a plurality of hollow members (e.g., pellets, pieces, tubes, etc.) that are at least partially coated with titanium dioxide ($TiO_2$). The hollow members are large enough to be retained within housing by bottom 84 and top 86 panels.

Lamp 44 is a light source that emits ultraviolet light (e.g., UV a, UV b, UV c, etc.). According to an exemplary embodiment, lamp 44 uses a 5 Watt (W) bulb (e.g., compact fluorescent). Alternatively, the bulb may be of any variety of sizes, power outputs or the like based on the desired performance of the environment. Lamp 44 cooperates with the catalyst to purify air passing through filter cartridge. Lamp 44 is coupled to an electrical contact 46 that is provided on the bottom of filter cartridge 32. Electrical contact 46 is configured to interface with a corresponding electrical interface 52 on base 34 to provide power to lamp 44. Ultraviolet light may weaken or otherwise damage polymer materials. Housing 40 is configured to substantially enclose lamp 44 so that most of the ultraviolet light emitted by lamp 44 does not escape housing 40. Access panel 38 and/or coupling mechanism 36 are also configured (e.g., shaped, positioned, orientated, etc.) to inhibit or prevent ultraviolet light from exiting the air treatment system. Filter cartridge 32 is removable and is able to be periodically replaced. According to various exemplary embodiments, spent filter cartridges may be disposed, recycled, or recharged. According to a preferred embodiment, lamp 44 does not provide a visible light outside of cartridge 32.

Figure 3:
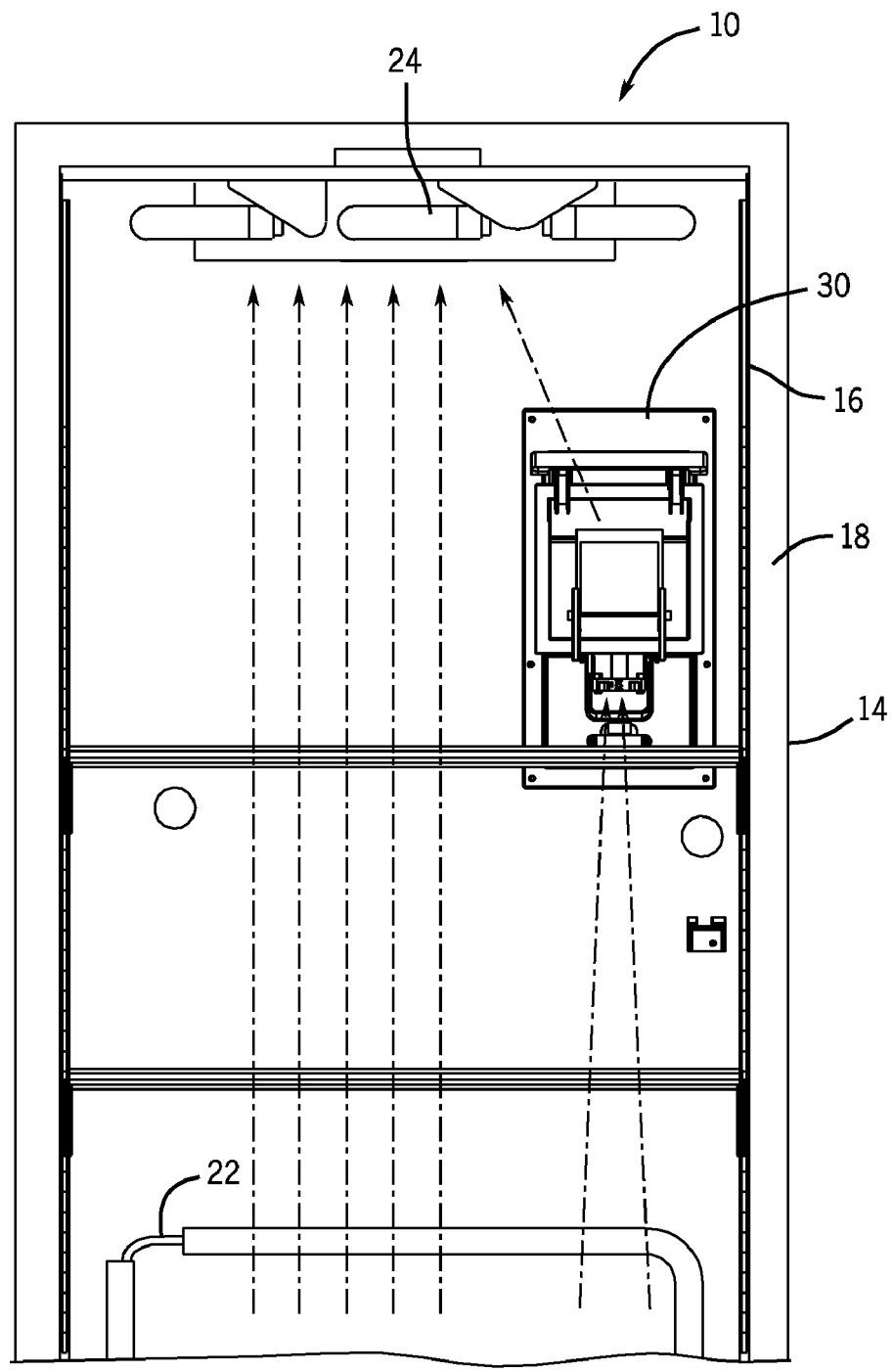
FIG. 3 is a front elevation view of a portion of the refrigerator in FIG. 1 with a portion of the inner wall hidden showing the airflow through the air duct between the evaporator and the evaporator fan according to an exemplary embodiment.
Figure 4:
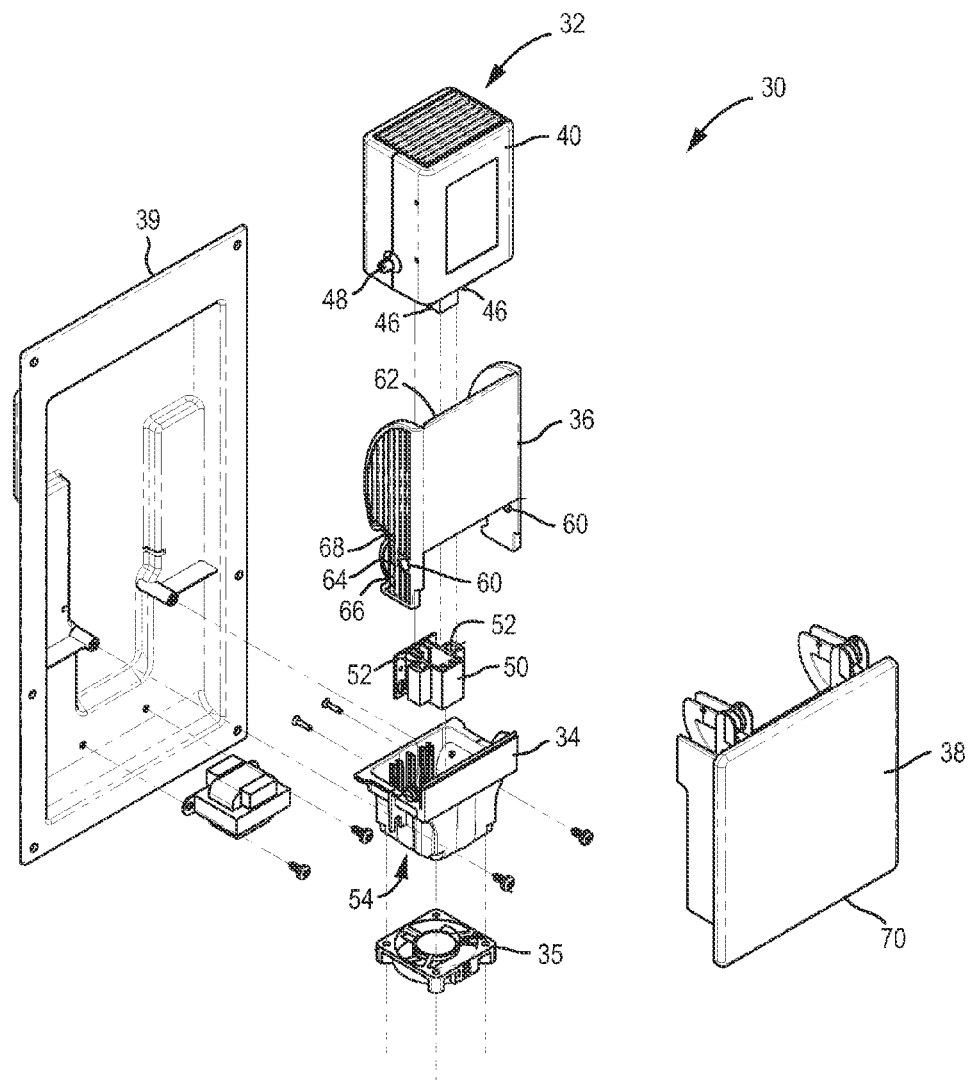
FIG. 4 is an exploded view of the air treatment system in FIG. 1 according to an exemplary embodiment.
Figure 5:
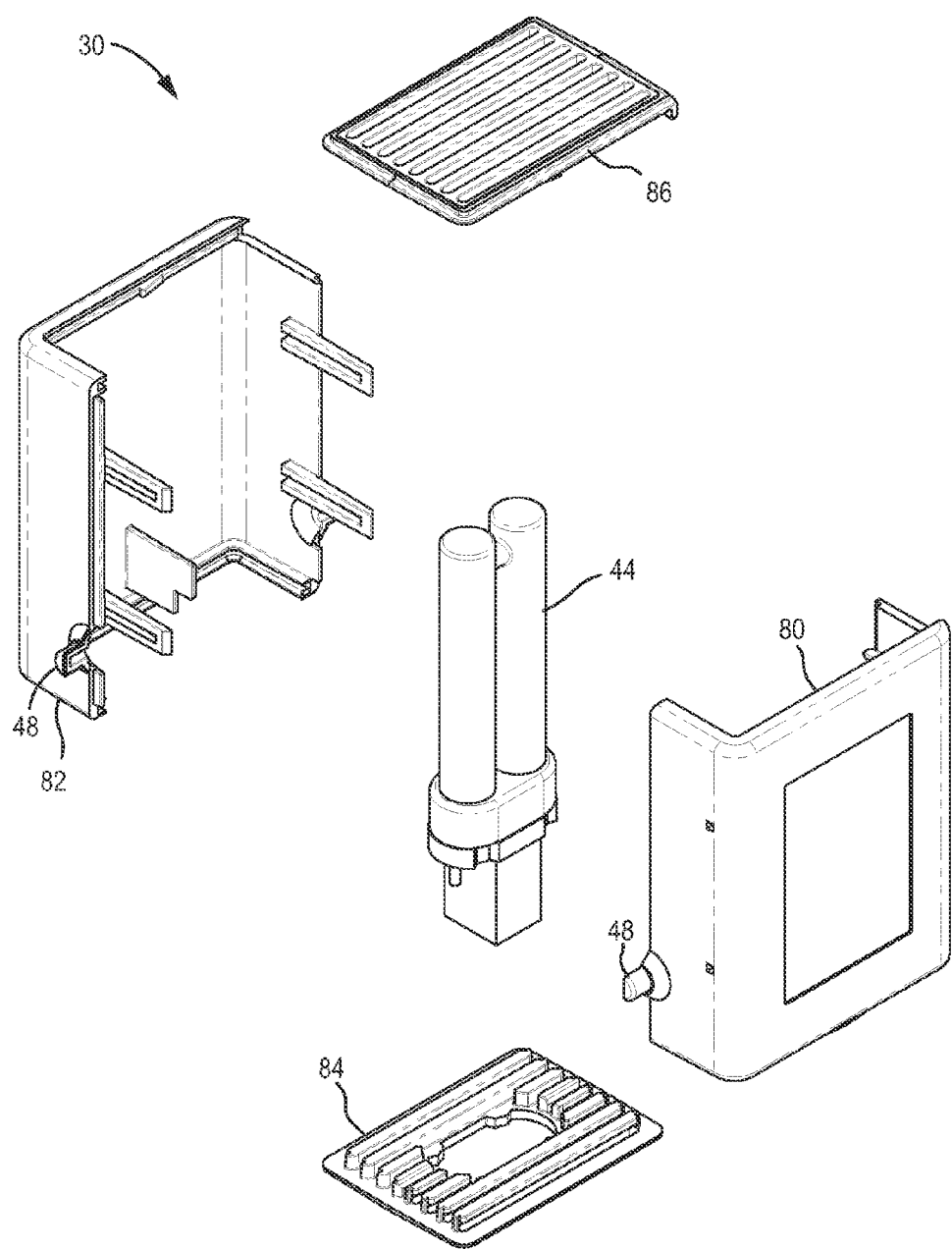
FIG. 5 is an exploded view of the filter cartridge in FIG. 4 according to an exemplary embodiment.

Filter cartridge 32 is coupled to base 34. Base 34 includes a receptacle or socket 50 that is configured to receive a portion of filter cartridge 32 and an electrical contact 52 within receptacle 50 that interfaces with electrical contact 46 to provide electrical power to lamp 44. Base 34 further forms an air duct 54 that allows air from air duct 18 to pass through base 34 and into filter cartridge 32. According to an exemplary embodiment, filter cartridge 32 is coupled to base 34 when it is fully seated within base 34. A second fan 35 is provided below base 34 to further direct air from air duct 18 into air treatment system 30. As shown in FIG. 3, air treatment system 30 only treats a portion of the air passing through air duct 18. Since air is being fairly continually circulated through air duct 18, all or substantially all of the air in refrigerator 10 will pass through air treatment system 30 over time.

Second fan 35 and base 34 are coupled to an external power source to provide electrical power to second fan 35, lamp 44, and any other components that may be included and draw electrical power (e.g., sensors, lights, etc.). According to one exemplary embodiment, electrical contacts 46 and 52 transfer electrical power between the refrigerator 10 and filter cartridge 32. According to other exemplary embodiments, the same or additional electrical contacts may transmit data between filter cartridge 32 and refrigerator 10 (e.g., data related to the life and/or performance of the filter cartridge).

A mounting or coupling mechanism 36 is provided to facilitate the coupling of filter cartridge 32 to base 34. Coupling mechanism 36 is coupled to base 34 at pivot points 60 and includes a lever 62 (e.g., release handle, lever, user interface, grip, etc.) with cam surfaces 64. Coupling mechanism 36 is moveable (e.g., pivot, rotate, swivel, swing, etc.) between a first or engaged position in which filter cartridge 32 is coupled to base 34 and a second or disengaged position in which filter cartridge 32 is released from base 34. A user may manipulate coupling mechanism 36 from cooled compartment 20 through an opening in inner wall 16 using lever 62 provided on a distal end of coupling mechanism 36 generally opposite of pivot points 60. Cam surfaces 64 are provided on coupling mechanism 36 and interface with projections 48

(e.g., protrusions, pegs, knobs, etc.) to engage and disengage filter cartridge 32 and base 34.

Figure 6A:
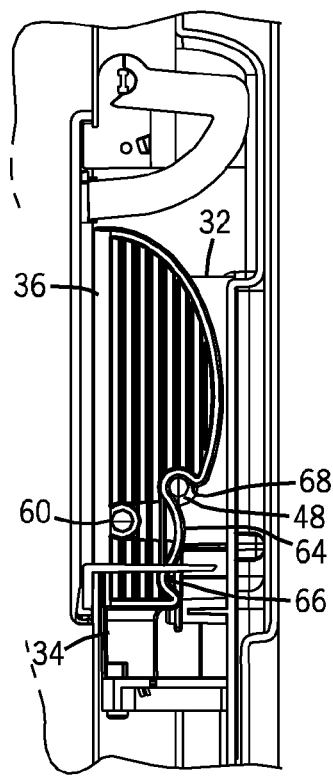
FIGS. 6A and 6B are side elevation views of the air treatment system in FIG. 1 in an first or closed position and a second or open position.
Figure 6B:
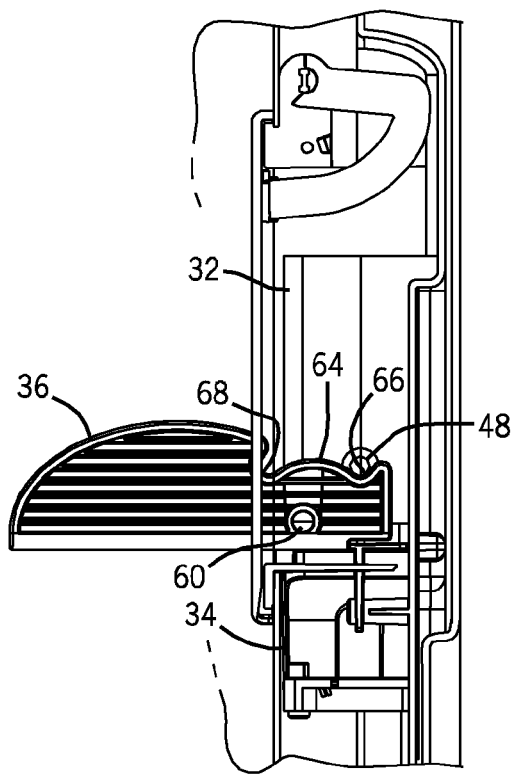
Figure 7A:
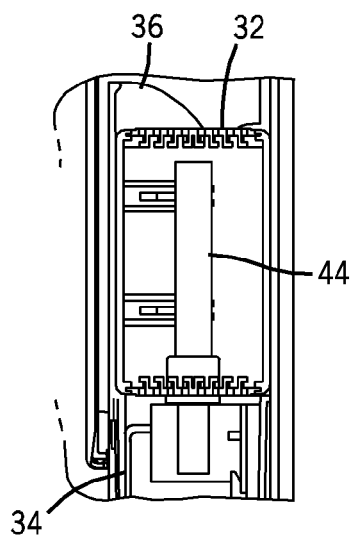
FIGS. 7A and 7B are cross-section views of the air treatment system in FIG. 1 in an first or closed position and a second or open position.
Figure 7B:
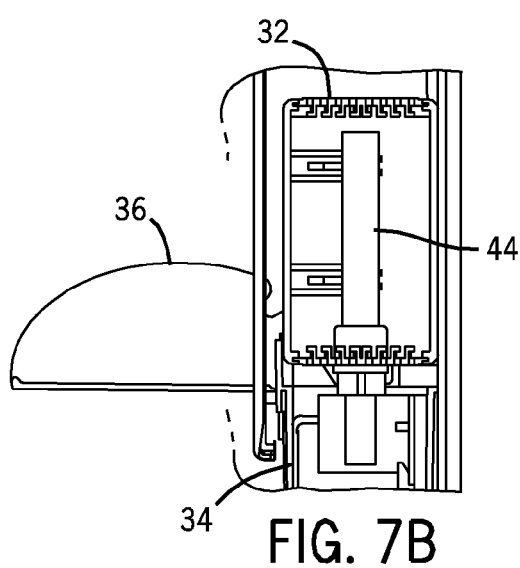

When coupling mechanism 36 is in a disengaged position (as shown in FIGS. 6B and 7B), filter cartridge 32 may be inserted into base 34. In this position, filter cartridge 32 is not coupled to base 34 and projections 48 sit in first seat 66. As coupling mechanism 36 is moved from an open position to a closed position, projections 48 ride along cam surfaces 64 until they are received in second seats 68. Filter cartridge 32 is pushed into a "snap-fit" with base 34 when coupling mechanism 36 is in a closed position and projections 48 are engaged with second seats 68 (as shown in FIGS. 6A and 7A). Coupling mechanism 36 ensures that filter cartridge is properly aligned with base 34 and fully seated in base 34 so that electrical contacts 46 and 52 are engaged. If filter cartridge 32 is not coupled properly to base 34, coupling mechanism 36 will remain in a position intermediate between the open position and closed position. This will prevent access panel 38 from closing and provide a visual indication that filter cartridge 32 is not properly installed.

To remove filter cartridge 32, a use grasps lever 62 and pulls coupling mechanism 36 to an open position. Projections 48 engage cam surfaces 64 and disengage filter cartridge 32 from base 34. When coupling mechanism 36 is in a disengaged position it lifts and presents filter cartridge 32 (e.g., to a user desiring to remove, check, replace, etc. filter cartridge 32).

Access panel 38 (e.g., door, hatch, etc.) is provided on inner surface of inner wall 16. Access panel 38 is pivotably coupled to inner wall 16 and is moveable between a first or open position in which air treatment system 30 is accessible from cooled compartment and a second or closed position in which air treatment system 30 is generally concealed from view. Access panel 38 includes an interface 70 (e.g., aperture, opening, detent, etc.) that facilitates the opening of access panel 38 by a user. According to an exemplary embodiment, access panel 38 pivots on hinges that are disposed along the upper edge of access panel 38. According to other exemplary embodiments, access panel may pivot along one of the sides or along the bottom edge.

Alternative Embodiments

Figure 8:
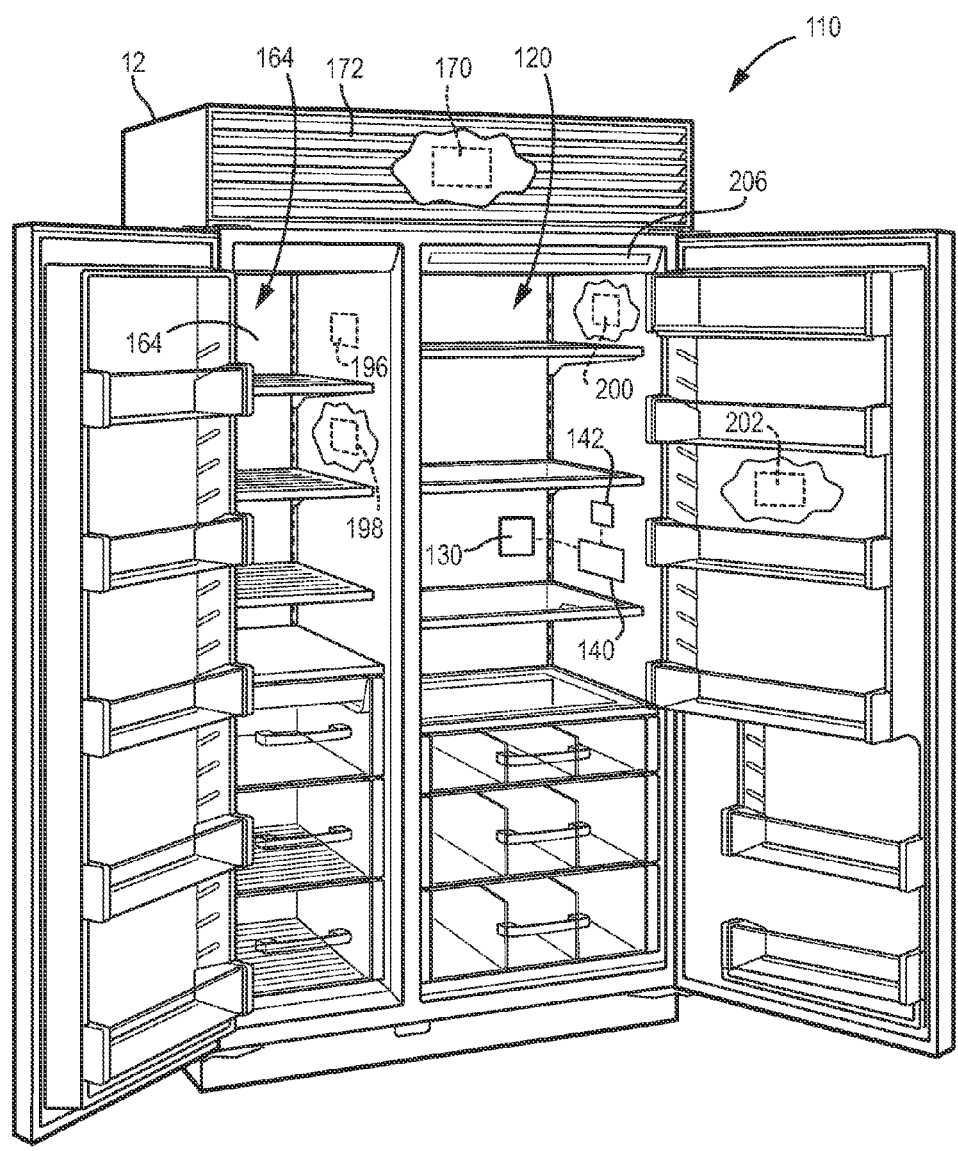
FIG. 8 is a perspective view of a storage compartment according to an alternative exemplary embodiment.

Referring to FIG. 8, a storage device or compartment 110 (e.g., a food storage compartment or device, a refrigerator, freezer, food pantry, etc.) is shown according to an alternative embodiment. Compartment 110 includes an enclosure 112 and an air treatment system 130, and may be a refrigerated (e.g., a refrigerator, a freezer, a refrigerator and freezer combination, etc.) or an unrefrigerated compartment or enclosure (e.g., a food storage compartment, pantry, cabinet, cupboard, etc.). According to various alternative embodiments, air treatment system 130 may be coupled to or located within compartment 110 at a variety of locations, as discussed in more detail herein.

Figure 9:
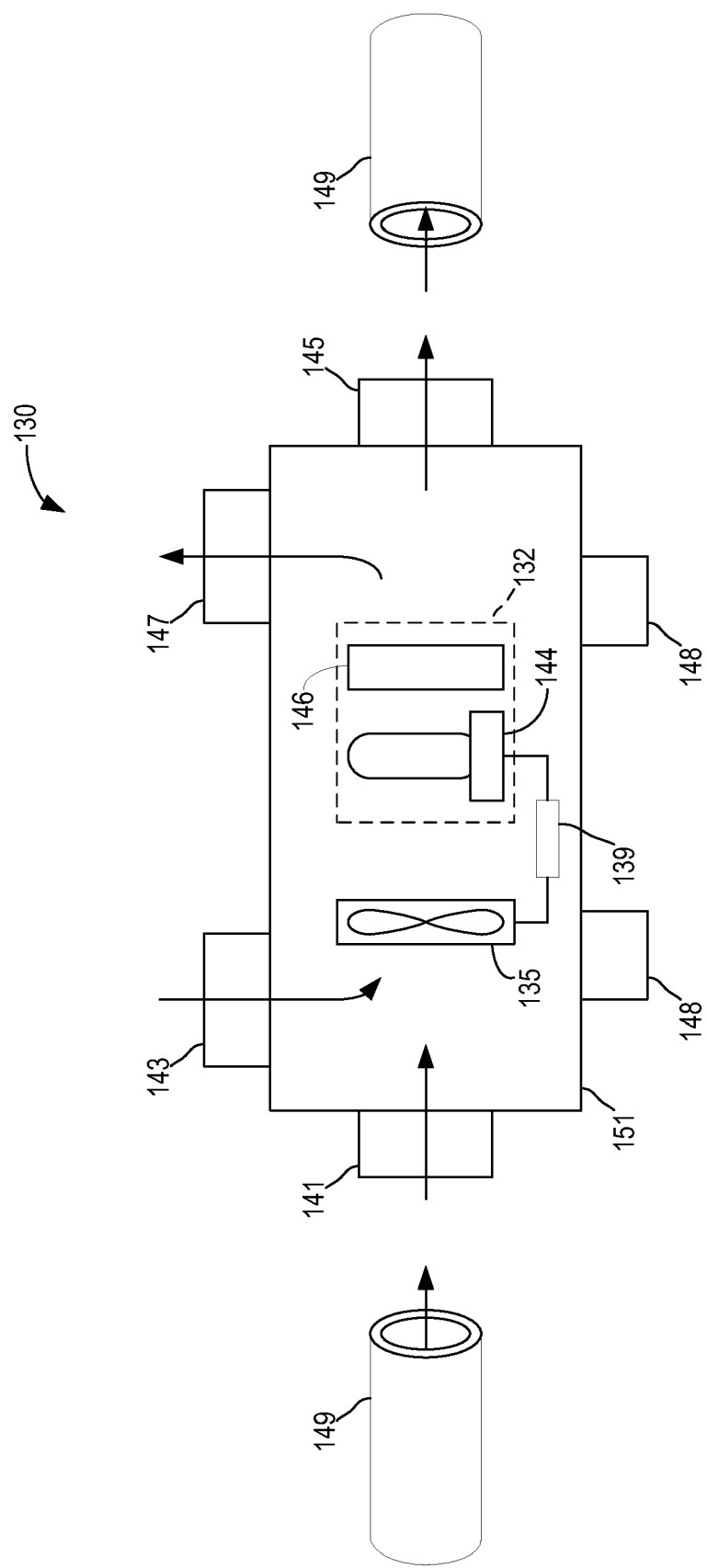
FIG. 9 is an illustration of an air treatment system according to an alternative exemplary embodiment.

Referring to FIG. 9, air treatment system 130 according to an exemplary embodiment is illustrated in greater detail. As shown in FIG. 9, air treatment system 130 includes a filter cartridge, or cartridge 132 provided within a housing 151. Housing 151 includes one or more air inlets 141, 143, and one or more air outlets 145, 147. The air inlets/outlets are configured to direct air through air treatment system 130 and cartridge 132. As shown in FIG. 9, cartridge 132 includes a light source or lamp 144 and a catalyst 146. According to various alternative embodiments, lamp 144 may be an ultraviolet light source (e.g., UV a, UV b, UV c, etc.), a light emitting diode (LED), or provide light having any of a wide range of wavelengths. Alternatively, lamp 144 may be of any variety of sizes, power outputs or the like based on the desired performance of cartridge 132. Lamp 144 cooperates with catalyst 146 to purify air passing through filter cartridge 132 in a similar fashion as discussed with respect to filter cartridge 32 and FIGS. 1-8. Air treatment system 130 is configured treat (e.g., purify, filter scrub, freshen, etc.) air inside refrigerator by oxidizing odor, bacteria, ethylene, volatile organic compounds (VOC's) or other undesirable particles without the use of ozone. According to an exemplary embodiment, air treatment system 130 is configured to react with ethylene to create carbon dioxide ($CO_2$) and/or water vapor ($H_2O$). Such ethylene is believed to be released from, among other sources, food products such as fruits and vegetables.

According to an exemplary embodiment, housing 151 may be configured (e.g., shaped, positioned, orientated, etc.) to inhibit or prevent ultraviolet light from exiting air treatment system 130. According to one embodiment, catalyst 146 is located within cartridge 132 at a distance of no more than approximately 4 inches from lamp 144. According to an alternative embodiment, catalyst 146 is provided as a coating on at least a portion of the exterior surface of lamp 144.

According to one embodiment, cartridge 132 is removable and is able to be periodically replaced. According to various exemplary embodiments, spent filter cartridges may be disposed, recycled, or recharged. For example, cartridge 130 may be removed and returned to, for example, a manufacturer, retailer, servicer, etc., and replaced with a different cartridge 130 that may be a new cartridge, or may be refurbished, recharged, recycled, etc. For example, cartridge 132 may use a catalyst that lasts a longer or shorter period of time than the light source such that the recycler can replace the spent component. According to yet another embodiment, lamp 144 may be replaceable independently from catalyst 146 in order to permit users to replace only lamp 144 rather than the entire filter cartridge 132.

According to an alternative embodiment, air treatment system 130 includes a fan 135. Fan 135 may be included as an alternate (e.g., a removable) component such that air treatment system 130 may operate either with or without fan 135. According to yet another alternative embodiment, air treatment system may be provided without fan 135, for example, in applications where air treatment system 130 is placed near or adjacent an air duct or fan such that air tends to flow through air treatment system 130 without the need for fan 135. According to one embodiment, fan 135 and/or cartridge 132 are independently removable components of air treatment system 130 such that one may be removed, replaced, etc. independent from the other.

As shown in FIG. 9, fan 135 and lamp 144 may be coupled to a power source 139. Power source 139 may comprise an internal power source such as a battery (e.g., a rechargeable battery, etc.) such that air treatment system 130 may operate independently from external power sources and not require a separate power line to be run to the air treatment system. According to one embodiment, power source 139 may be provided as a removable component of air treatment system 130 (e.g., a removable, replaceable, and/or rechargeable battery). According to yet another embodiment, power source 139 may be a power coupling (e.g., an electrical plug, an electrical contact, etc.) configured to be electrically coupled to an external power source such as a wall outlet, the power system of compartment 110, etc. According to yet another embodiment, air treatment system 130 may be configured to be selectively powered by both an internal power source such as a battery and an external power source such as the power system of compartment 110.

According to one embodiment, air treatment system 130 is configured to run on a continuous basis. Referring to FIG. 8, according to various alternative embodiments, the operation of air treatment system 130 may be controlled by a control system 140 that includes a control system input device 142. Control system 140 controls (e.g., turns on/off) air treatment system 130 based upon inputs provided by control system input device 142. According to one embodiment, device 142 may be configured by a user such that air treatment system 130 runs according to user preferences. User preferences may include periods of time (e.g., certain times of day, etc.), air quality, etc. Further, device 142 may be configured as or with one or more sensors that detect operational conditions of compartment 11 0, such as whether a door included with compartment 110 is open, whether the levels of certain compounds, such as ethylene, are above or below certain levels or within a certain range, etc. For example, device 142 may include a sensor that indicates when a crisper drawer is in the open/closed positions, or when a refrigerator door is open, etc. Other parameters may be taken into account by device 142 and control system 140 according to various alternative embodiments in controlling the operation of air treatment system 130. According to one embodiment, device 142 includes input features (e.g., buttons, etc.) that are integrated into a display panel 206 (see FIG. 8). According to various embodiments, control system 140 and device 142 may be located in a wide variety of locations.

Figure 11:
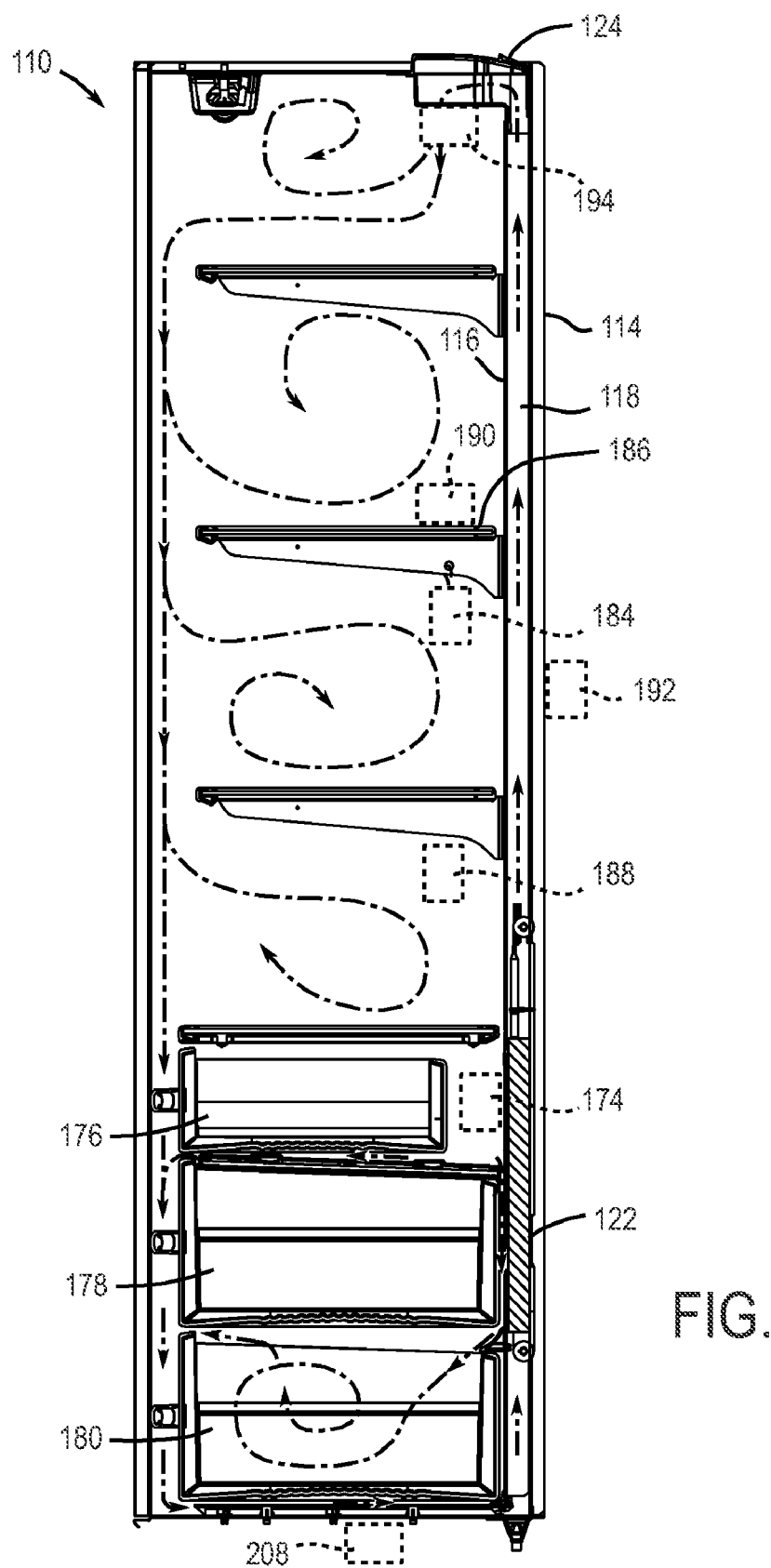
FIG. 11 is a cross-section view of the storage compartment of FIG. 8 according to an exemplary embodiment.

Referring now to FIG. 11, according to one embodiment, compartment 110 may be a refrigerated compartment and include an evaporator 122 and an evaporator fan 124. Enclosure 112 forms the main body of compartment 110 and includes an outer wall 114 (e.g., an insulated wall, an uninsulated wall, etc.) and an inner wall 116 (e.g., cold plate, etc.). Enclosure 112 may be a refrigerator compartment (e.g., for fresh foods) or a freezer compartment (e.g., for frozen foods), or alternatively, enclosure 112 may be used in a variety of unrefrigerated applications.

According to one embodiment, outer wall 114 and inner wall 116 are at least partially separated by (or together define) an air duct 118 (e.g., passage, space, volume, passageway, etc.). Inner wall 116 defines a space 120 (e.g., a cooled area, space, etc.) that is configured to receive and store items (e.g., food items to be stored). According to an alternative embodiment, space 120 is cooled by a refrigeration system that includes at least a compressor, evaporator 122, and evaporator fan 124. According to an exemplary embodiment, evaporator 122 is disposed at least partially in air duct 118 and generally towards the bottom of enclosure 112. Evaporator fan 124 is disposed towards the top of enclosure 112 and draws air from evaporator 122, upwards through air duct 118 and into space 120. According to various alternative embodiments, evaporator 122 and/or evaporator fan 124 may be located in any suitable location(s).

Figure 10:
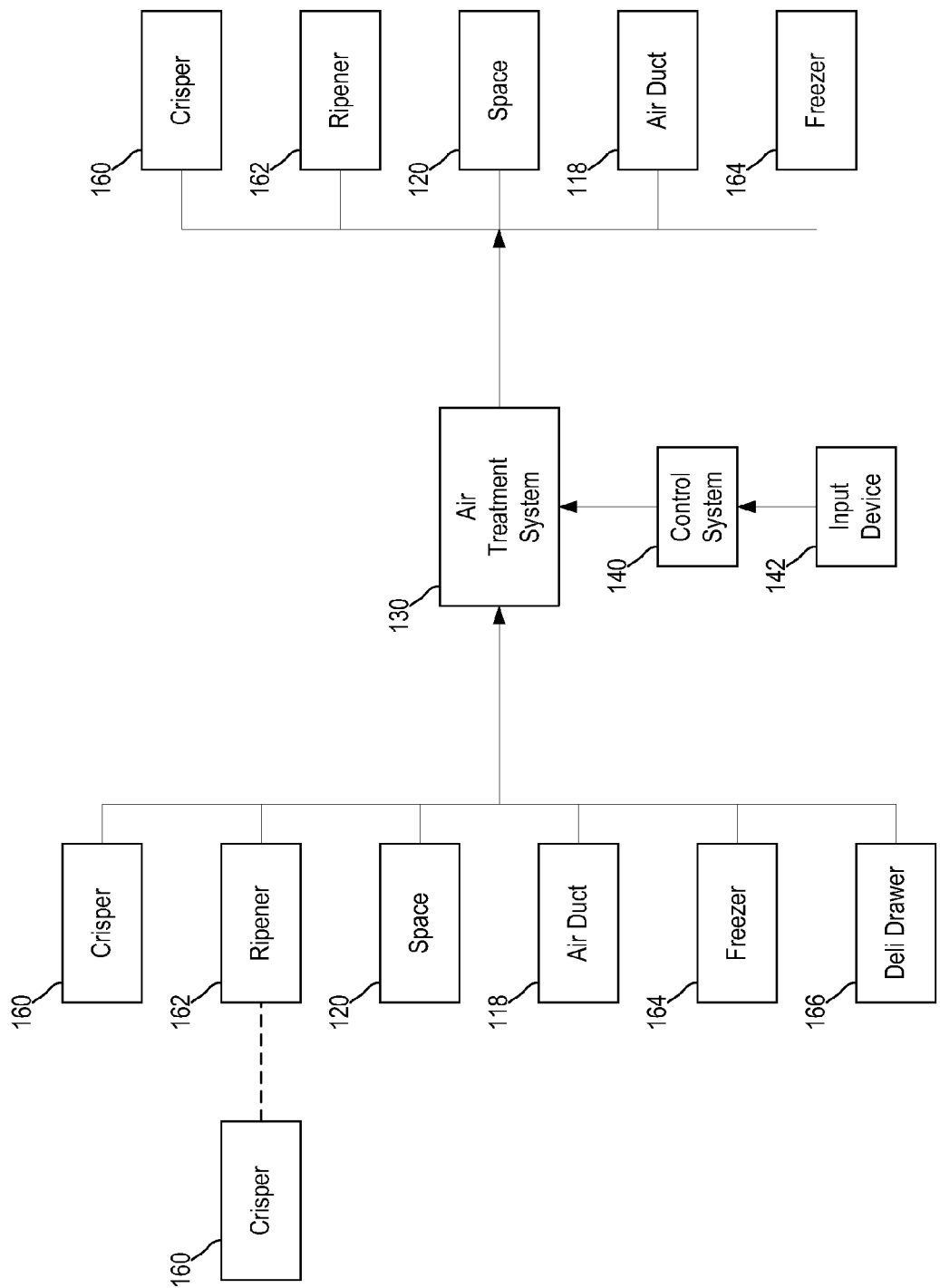
FIG. 10 is a block diagram illustrating airflow pathways through the storage compartment of FIG. 8 according to an exemplary embodiment.

According to various alternative embodiments, air treatment system 130 may receive air from and release air to a variety of locations. Referring now to FIG. 10, a block diagram illustrating a number of exemplary input locations and output locations for air treatment system 130 is shown according to an exemplary embodiment. As shown in FIG. 10, air treatment system 130 may receive air from, among other sources, a crisper area or drawer 160 (e.g., a crisper space), a ripener area or drawer 162 (which in turn, may receive air from a crisper drawer similar to, e.g., drawer 178 shown in FIG. 11), space 120, air duct 118, a freezer 164, and/or a deli drawer 166 (e.g., a drawer for storing meats, cheeses, etc.). Air treatment system 130 may outlet air to, among other places, crisper area or drawer 160, air duct 118, space 120, ripener area or drawer 162, and/or freezer 164. Air treatment system 130 may be located within compartment 110 such that it receives air from one or more of the inlet sources shown in FIG. 10 and, after treating the air, outlets the treated air to one or more of the outlet locations shown in FIG. 10. Other inlet/outlet locations may be utilized in combination with air treatment system 130 according various alternative embodiments. Air treatment system 130 may include a dedicated air duct or conduit that is separate from a main or primary air duct used to move air through, for example, a cooling system (e.g., over an evaporator etc.) used to cool compartment 110. In order to move air between the various inlets/outlets, additional ducting 149 may be required to be coupled to one or both of inlets 141, 143 and outlets 145, 147 of air treatment system 130. Ducting 149 may take any suitable form and/or shape and be made of any suitable material according to various alternative embodiments.

For example, referring back to FIG. 8, according to one embodiment, air treatment system 130 may be located above space 120 at a location 170 and be enclosed within the upper portion of compartment 110 (e.g., behind a grill member 172 as shown in FIG. 8). Because such a location may not be not in line with duct 118 or adjacent an existing fan, one or more sections of additional ducting 149 (see FIG. 9) and/or fan 135 may be required to guide and/or move air from an inlet location (e.g., duct 118) to an outlet location (e.g., space 120).

According to another embodiment, air treatment system 130 may be configured to service one or more drawers within compartment 110. For example, air treatment system 130 may be provided at location 174 shown in FIG. 11 and be configured to treat air that is drawn from one or more of drawers 176, 178, 180. According to one embodiment, a separate air treatment system 130 may be provided for each of drawers 176, 178, 180. According to another embodiment, one or more drawers may be substantially sealed off from the remainder of space 120 such that air treatment system 130 may primarily treat air circulated only through the drawers. This may be particularly useful if one or more of drawers 176, 178, 180 is used as a crisper drawer (e.g., a drawer intended to be used to store fruits, vegetables, etc.) because the main source of ethylene is often from fruits and vegetables. According to one embodiment, one or more of drawers 176, 178, 180 may include or be coupled to additional ducting 149 (e.g., coupled to a side or bottom surface) such that air may be drawn from the drawer and guided toward air treatment system 130 (e.g., the ducting may be configured similar to the conduit(s) used to supply water/fluid to a typical dishwasher spray arm underneath a middle/upper dishwasher rack/basket, but be used instead to guide air from a drawer or other space within a refrigerator, etc.). According to another embodiment, the additional ducting 149 may be positioned or coupled to one or more drawers 176, 178, 180 such that additional ducting 149 docks with (e.g., engages, couples with, etc.) a channel (e.g., additional ducting 149) to guide the air to air treatment system 130. According to another embodiment, separate additional ducting 149 may be used to move air between evaporator 122 and one or more crispers (e.g., such as 176) via air treatment system 130. According to one embodiment, air treatment system 130 may draw air from a crisper drawer (e.g., such as drawer 178) that in turn travels through a ripener drawer (e.g., such as drawer 176) prior to treating the air (e.g., via a channel 182). This may facilitate ripening of food products stored in a ripener drawer by providing an extra source of ethylene (e.g., from a drawer such as drawer 178 being used as a crisper drawer to store fruits and vegetables).

According to yet another embodiment, air treatment system 130 may be an independent component that may be placed within (e.g., exposed in a similar manner to a filter used in many typical refrigerators) or secured to a portion of compartment 110. For example, as shown in FIG. 11 at location 184, air treatment system 130 may be hung from a shelf 186. Alternatively, air treatment system 130 may be secured to a sidewall (see location 188), rest on shelf 186 (see location 190), or be mounted from the exterior of compartment 110 (see location 192). Further, air treatment system 130 may be located adjacent evaporator fan 124, e.g., at location 194, be within a freezer compartment (see location 196), or be within one or more walls of compartment 110 (see locations 198, 200, 202). Further yet, air treatment system 130 may be located below compartment 110 at, for example, location 208. In order to accommodate the various locations and applications, air treatment system 130 may be provided with or without one or more of inlets 141, 143 and outlets 145, 147 (e.g., to accommodate straight-line airflow through air treatment system 130, "U" directional air flow, right-angle air flow, etc.). Further, additional ducting 149 and/or fan 135 may be required to guide and/or move air through air treatment system 130 depending on the specific location and surrounding environment. According to yet another embodiment, air treatment system may be configured to operate in conjunction with a refrigerator/freezer combination that uses cooled air from the freezer as the primary and/or sole source for cooled air that is sent to the refrigerator.

Referring back to FIG. 9, according to various alternative embodiments, air treatment system 130 may be provided with a mounting member 148, which may comprise one or more screws, bolts, adhesives, hook/loop fasteners, suction devices, hanging hooks (e.g., clips, etc.), or a variety of other connecting members suitable for mounting air treatment system 130.

It should be understood that the embodiments described herein are exemplary only and are not exhaustive of the different types of configurations that may be utilized in combination with air treatment system 130. Configurations utilizing different locations for the inlets/outlets and/or air treatment system 130 are to be considered within the scope of the present disclosure.

Figure 12:
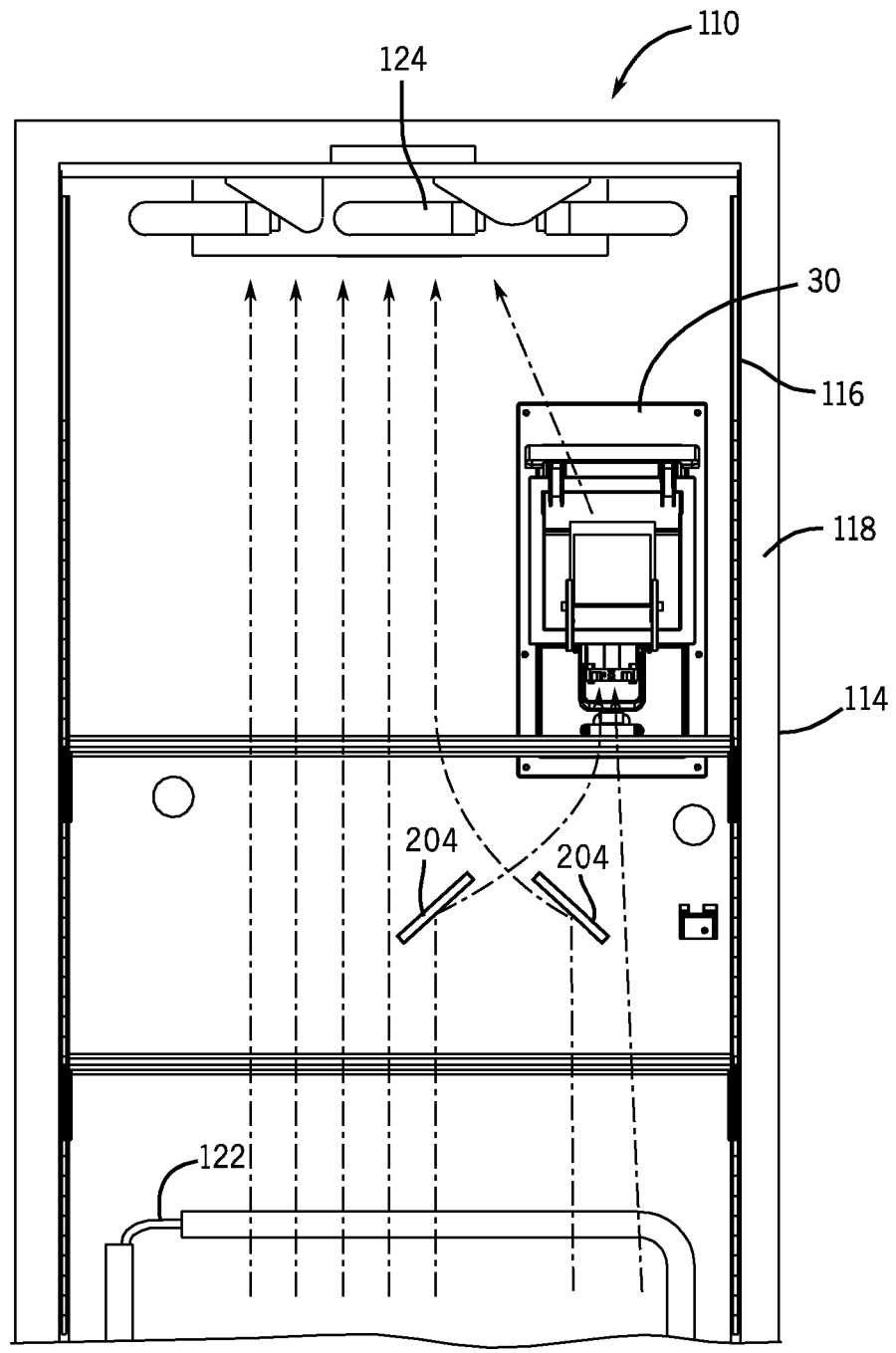
FIG. 12 is a front elevation view of a portion of the refrigerator in FIG. 8 with a portion of the inner wall hidden showing the airflow according to an alternative exemplary embodiment.

Referring now to FIG. 12, according to an alternative embodiment, one or more baffles 204 (e.g., ribs, projections, etc.) may be provided within duct 118 in order to redirect the airflow through duct 118. Baffles 204 may be secured to one or both of walls 114, 116. As shown in FIG. 12, one or more baffles 204 may be provided upstream from air treatment system 130 such that air is directed both toward and away from air treatment system 130. In this way, baffles 204 are intended to ensure that over the course of operation, all of the air flowing through compartment 110 and air duct 118 eventually is treated by air treatment system 130. While baffles 204 are shown as being oriented diagonally to the airflow upstream of air treatment system 130, according to various alternative embodiments, baffles 204 may be oriented in a variety of positions and be located downstream from air treatment system 130.

For purposes of this disclosure, the term "coupled" shall mean the joining of two members directly or indirectly to one another. Such joining may be stationary in nature or movable in nature. Such joining may be achieved with the two members or the two members and any additional intermediate members being integrally formed as a single unitary body with one another or with the two members or the two members and any additional intermediate member being attached to one another. Such joining may be permanent in nature or alternatively may be removable or releasable in nature. Such joining may also relate to mechanical, fluid, or electrical relationship between the two components.

It is also important to note that the construction and arrangement of the elements of the refrigerator as shown in the preferred and other exemplary embodiments are illustrative only. Although only a few embodiments of the present invention have been described in detail in this disclosure, those skilled in the art who review this disclosure will readily appreciate that many modifications are possible (e.g., variations in sizes, dimensions, structures, shapes and proportions of the various elements, values of parameters, mounting arrangements, materials, colors, orientations, etc.) without materially departing from the novel teachings and advantages of the subject matter recited in the claims. For example, air treatment is intended to broadly relate to a variety of conditioning of air within a compartment, appliance, etc., including filtering, purifying, scrubbing, freshening, and the like. Accordingly, all such modifications are intended to be included within the scope of the present invention as defined in the appended claims. The order or sequence of any process or method steps may be varied or re-sequenced according to alternative embodiments. In the claims, any means-plus-function clause is intended to cover the structures described herein as performing the recited function and not only structural equivalents but also equivalent structures. Other substitutions, modifications, changes and/or omissions may be made in the design, operating conditions and arrangement of the preferred and other exemplary embodiments without departing from the spirit of the present invention as expressed in the appended claims.

What is claimed is:

1. A storage compartment comprising:
   an enclosure defining a storage space;
   an air treatment system in fluid communication with the storage space, the air treatment system comprising a housing and a removeable cartridge provided within the housing, the removeable cartridge comprising a light source and a catalyst and configured to treat air;
   an air duct in communication with the enclosure; and
   a fan configured to move air between the air treatment system and the enclosure;
   wherein the removeable cartridge comprises the fan.

2. The storage compartment of claim 1, wherein the light source comprises an ultraviolet light source and the catalyst comprises a titanium dioxide-coated catalyst.

3. The storage compartment of claim 1, wherein the light source is a light emitting diode.

4. The storage compartment of claim 1, further comprising:
   a control system coupled to both the air treatment system and a control system input;
   wherein the control system controls the operation of the air treatment system based upon an input received from the control system input.

5. The storage compartment of claim 4, wherein the input is a period of time.

6. The storage compartment of claim 4, wherein the enclosure comprises a door defining the storage space, and the input includes an indication of a position of the door.

7. The storage compartment of claim 1, wherein the enclosure is a drawer within a refrigerated compartment.

8. The storage compartment of claim 1, wherein the enclosure is a freezer compartment.

9. The storage compartment of claim 1, further comprising a connecting member configured to removably couple the air treatment system to the enclosure.

10. The storage compartment of claim 1, wherein the enclosure is a refrigerator, freezer, combination refrigerator/freezer, cabinet, or pantry.

11. An air treatment system for an appliance comprising:
a housing comprising an inlet and an outlet and defining a conduit;
a light source provided within the housing;
a catalyst provided within the housing;
a connector configured to removably couple the housing to the appliance; and
a cartridge comprising the light source and the catalyst;
wherein the cartridge is removable from the housing and comprises a fan configured to move air from the inlet to the outlet.

12. The air treatment system of claim 11, wherein the light source activates the catalyst to treat air moved through the conduit without the use of ozone.

13. The air treatment system of claim 11, wherein the light source is an ultraviolet light source and the catalyst is a titanium dioxide-coated catalyst.

14. The air treatment system of claim 11, further comprising a panel removable to access the catalyst for inspection, repair, or replacement.

15. The air treatment system of claim 11, further comprising a fan configured to move air in to, out of, and/or through the conduit.

16. The air treatment system of claim 15, wherein the fan is mounted inside the housing.

17. The air treatment system of claim 11, wherein the light source is readily removable for inspection, repair, or replacement.

18. The air treatment system of claim 11, further comprising a battery configured to provide power to at least the light source.

19. The air treatment system of claim 11, wherein the connector mechanically and electrically removably couples to the appliance.

* * * * *